(12) United States Patent
Ferko et al.

(10) Patent No.: US 11,278,416 B2
(45) Date of Patent: Mar. 22, 2022

(54) CONCENTRIC KEEL TKA

(71) Applicant: Howmedica Osteonics Corp., Mahwah, NJ (US)

(72) Inventors: Michael C. Ferko, Warwick, NY (US); Peter Wellings, Somerset, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 79 days.

(21) Appl. No.: 16/683,642

(22) Filed: Nov. 14, 2019

(65) Prior Publication Data

US 2021/0145592 A1    May 20, 2021

(51) Int. Cl.
*A61F 2/38*    (2006.01)
*A61F 2/30*    (2006.01)

(52) U.S. Cl.
CPC ........ *A61F 2/3859* (2013.01); *A61F 2/30749* (2013.01); *A61F 2002/30301* (2013.01); *A61F 2002/30471* (2013.01); *A61F 2002/30889* (2013.01); *A61F 2002/30891* (2013.01); *A61F 2002/30892* (2013.01); *A61F 2002/3863* (2013.01)

(58) Field of Classification Search
CPC ................ A61F 2/3859; A61F 2/30759; A61F 2002/30889
See application file for complete search history.

(56) References Cited

U.S. PATENT DOCUMENTS

| | | |
|---|---|---|
| 4,085,466 A | 4/1978 | Goodfellow et al. |
| RE29,757 E | 9/1978 | Helfet |
| 4,232,404 A | 11/1980 | Samuelson et al. |
| 4,385,405 A | 5/1983 | Teinturier |
| 4,550,448 A | 11/1985 | Kenna |
| 4,986,833 A | 1/1991 | Worland |
| 5,236,461 A | 8/1993 | Forte |
| 5,417,693 A | 5/1995 | Sowden et al. |
| 5,593,448 A | 1/1997 | Dong |
| 5,743,910 A | 4/1998 | Bays et al. |
| 5,755,803 A | 5/1998 | Haines et al. |
| 5,800,552 A | 9/1998 | Forte |

(Continued)

FOREIGN PATENT DOCUMENTS

| | | |
|---|---|---|
| EP | 0028546 A1 | 5/1981 |
| FR | 2836821 A1 | 9/2003 |

(Continued)

OTHER PUBLICATIONS

International Search Report and written opinion for Application No. PCT/US2012/043780 dated Aug. 23, 2012.

(Continued)

*Primary Examiner* — Marcia L Watkins
(74) *Attorney, Agent, or Firm* — Lerner, David, Littenberg, Krumholz & Mentlik, LLP (57) ABSTRACT

Disclosed herein are implants with pivots that can be rotated about these pivots to be implanted onto bone, and methods for implanting same. The implant may have a plurality of pivot pads and curved projections extending from one or more bone contacting surfaces. The pivot pads and curved projections may engage with corresponding features on bone for implantation and securement of the implant to the bone. The implant may be rotated about the plurality of pivot pads placed in corresponding recesses on bone to seat the projections into the corresponding recesses.

15 Claims, 8 Drawing Sheets

(56) References Cited

U.S. PATENT DOCUMENTS

| | | | |
|---|---|---|---|
| 5,824,100 | A | 10/1998 | Kester et al. |
| 5,928,232 | A | 7/1999 | Howland et al. |
| 5,971,946 | A | 10/1999 | Quinn et al. |
| 5,989,259 | A | 11/1999 | Penenberg et al. |
| 6,102,955 | A | 8/2000 | Mendes et al. |
| 6,110,179 | A | 8/2000 | Flivik et al. |
| 6,165,221 | A | 12/2000 | Schmotzer |
| 6,197,064 | B1 | 3/2001 | Haines et al. |
| 6,204,620 | B1 | 3/2001 | McGee et al. |
| 6,313,595 | B2 | 11/2001 | Swanson et al. |
| 6,322,567 | B1 | 11/2001 | Mittelstadt et al. |
| 6,364,910 | B1 | 4/2002 | Shultz et al. |
| 6,540,786 | B2 | 4/2003 | Chibrac et al. |
| 6,612,449 | B1 | 9/2003 | Otani et al. |
| 6,676,669 | B2 | 1/2004 | Charles et al. |
| 6,702,805 | B1 | 3/2004 | Stuart |
| 6,723,106 | B1 | 4/2004 | Charles et al. |
| 6,757,582 | B2 | 6/2004 | Brisson et al. |
| 6,916,341 | B2 | 7/2005 | Rolston |
| 6,953,479 | B2 | 10/2005 | Carson et al. |
| 7,035,716 | B2 | 4/2006 | Harris et al. |
| 7,160,330 | B2 | 1/2007 | Axelson, Jr. et al. |
| 7,258,701 | B2 | 8/2007 | Aram et al. |
| 7,294,149 | B2 | 11/2007 | Hozack et al. |
| 7,387,644 | B2 | 6/2008 | Beynnon et al. |
| 7,458,991 | B2 | 12/2008 | Wang et al. |
| 7,465,320 | B1 | 12/2008 | Kito et al. |
| 7,520,901 | B2 | 4/2009 | Engh et al. |
| 7,524,334 | B2 | 4/2009 | Haidukewych |
| 7,537,664 | B2 | 5/2009 | O'Neill et al. |
| 7,544,209 | B2 | 6/2009 | Lotke |
| 7,578,850 | B2 | 8/2009 | Kuczynski et al. |
| 7,582,118 | B2 | 9/2009 | Brown et al. |
| 7,618,451 | B2 | 11/2009 | Berez et al. |
| 7,628,817 | B1 | 12/2009 | Axelson, Jr. et al. |
| 7,674,426 | B2 | 3/2010 | Grohowski, Jr. |
| 7,708,782 | B2 | 5/2010 | Burstein et al. |
| 7,725,162 | B2 | 5/2010 | Malackowski et al. |
| 7,766,913 | B2 | 8/2010 | Bennett et al. |
| 7,831,292 | B2 | 11/2010 | Quaid et al. |
| 7,892,243 | B2 | 2/2011 | Stuart |
| 7,935,150 | B2 | 5/2011 | Carignan et al. |
| 8,002,777 | B2 | 8/2011 | Fox et al. |
| 8,004,229 | B2 | 8/2011 | Nowlin et al. |
| 8,010,180 | B2 | 8/2011 | Quaid et al. |
| 8,172,775 | B2 | 5/2012 | Warkentine et al. |
| 8,287,545 | B2 | 10/2012 | Haines |
| 8,317,869 | B2 | 11/2012 | Cloutier et al. |
| 8,353,914 | B2 | 1/2013 | Haines |
| 8,366,783 | B2 | 2/2013 | Samuelson et al. |
| 8,496,663 | B2 | 7/2013 | White et al. |
| 8,784,497 | B2 | 7/2014 | Samuelson et al. |
| 8,911,501 | B2 | 12/2014 | Irwin et al. |
| 8,998,915 | B2 | 4/2015 | Fitz et al. |
| 9,055,953 | B2 | 6/2015 | Lang et al. |
| 9,326,780 | B2 | 5/2016 | Wong et al. |
| 9,339,391 | B2 | 5/2016 | Samuelson et al. |
| 9,381,085 | B2 | 7/2016 | Axelson, Jr. et al. |
| 9,517,134 | B2 | 12/2016 | Lang |
| 9,579,216 | B2 | 2/2017 | Axelson, Jr. et al. |
| 2001/0018597 | A1 | 8/2001 | Gellman et al. |
| 2001/0031937 | A1 | 10/2001 | Repice et al. |
| 2003/0005786 | A1 | 1/2003 | Stuart et al. |
| 2004/0167630 | A1 | 8/2004 | Rolston |
| 2005/0125068 | A1 | 6/2005 | Hozack et al. |
| 2005/0154471 | A1 | 7/2005 | Aram et al. |
| 2006/0030855 | A1 | 2/2006 | Haines |
| 2006/0058882 | A1 | 3/2006 | Haines |
| 2006/0116772 | A1 | 6/2006 | Haidukewych |
| 2006/0147332 | A1 | 7/2006 | Jones et al. |
| 2006/0178748 | A1 | 8/2006 | Dinger et al. |
| 2006/0195195 | A1 | 8/2006 | Burstein et al. |
| 2006/0228247 | A1 | 10/2006 | Grohowski |
| 2007/0100462 | A1 | 5/2007 | Lang et al. |
| 2008/0119938 | A1 | 5/2008 | Oh |
| 2008/0183177 | A1 | 7/2008 | Fox et al. |
| 2008/0188942 | A1 | 8/2008 | Brown et al. |
| 2008/0202274 | A1 | 8/2008 | Stuart |
| 2008/0262626 | A1 | 10/2008 | Raugel |
| 2009/0198340 | A1 | 8/2009 | Cloutier et al. |
| 2010/0094429 | A1 | 4/2010 | Otto |
| 2010/0222781 | A1 | 9/2010 | Collazo et al. |
| 2010/0268249 | A1 | 10/2010 | Stuart |
| 2010/0268250 | A1 | 10/2010 | Stuart et al. |
| 2010/0275718 | A1 | 11/2010 | Stuart et al. |
| 2010/0292804 | A1 | 11/2010 | Samuelson |
| 2010/0312348 | A1 | 12/2010 | Wang et al. |
| 2011/0054626 | A1 | 3/2011 | Thomas et al. |
| 2011/0087332 | A1 | 4/2011 | Bojarski et al. |
| 2011/0144760 | A1 | 6/2011 | Wong et al. |
| 2011/0238073 | A1 | 9/2011 | Lang et al. |
| 2011/0251694 | A1 | 10/2011 | Wasielewski |
| 2012/0109324 | A1 | 5/2012 | Keggi et al. |
| 2012/0330429 | A1 | 12/2012 | Axelson, Jr. et al. |
| 2013/0211531 | A1 | 8/2013 | Steines et al. |
| 2013/0317523 | A1 | 11/2013 | Borus |
| 2014/0039520 | A1 | 2/2014 | Haider et al. |
| 2014/0163688 | A1 | 6/2014 | Abidi et al. |
| 2014/0228860 | A1 | 8/2014 | Steines et al. |
| 2015/0032215 | A1 | 1/2015 | Slamin et al. |
| 2015/0057756 | A1 | 2/2015 | Lang et al. |
| 2015/0351940 | A1 | 12/2015 | Lacraz |
| 2016/0008143 | A1 | 1/2016 | Mahfouz |
| 2016/0038293 | A1 | 2/2016 | Slamin et al. |
| 2016/0143744 | A1 | 5/2016 | Bojarski et al. |
| 2016/0158019 | A1 | 6/2016 | Grey et al. |
| 2016/0199198 | A1 | 7/2016 | Dietz et al. |
| 2016/0220379 | A1 | 8/2016 | Parisi et al. |
| 2016/0235541 | A1 | 8/2016 | Samuelson et al. |
| 2016/0242919 | A1 | 8/2016 | Engh et al. |
| 2016/0242931 | A1 | 8/2016 | Wong et al. |
| 2016/0262910 | A1 | 9/2016 | Axelson, Jr. et al. |
| 2016/0270854 | A1 | 9/2016 | Chaoui |
| 2016/0302933 | A9 | 10/2016 | Haines |
| 2016/0317309 | A1 | 11/2016 | Al Hares et al. |
| 2016/0324581 | A1 | 11/2016 | Bojarski et al. |
| 2016/0324646 | A1 | 11/2016 | Carignan et al. |
| 2016/0331386 | A1 | 11/2016 | Axelson, Jr. et al. |
| 2016/0367373 | A1 | 12/2016 | Samuelson et al. |
| 2017/0014140 | A1 | 1/2017 | Samuelson et al. |

FOREIGN PATENT DOCUMENTS

| | | |
|---|---|---|
| JP | H01244748 A | 9/1989 |
| WO | 03007852 A1 | 1/2003 |
| WO | 2011072235 A2 | 6/2011 |
| WO | 2012126496 A1 | 9/2012 |

OTHER PUBLICATIONS

U.S. Appl. No. 61/530,614, filed Nov. 16, 2011.
European Search Report for Application No. EP 20206838, dated Apr. 1, 2021, 8 pages.

CONCENTRIC KEEL TKA

FIELD OF THE INVENTION

The present invention relates to implants and surgical methods for artificial joint replacement, and in particular relates to an implant with a plurality of pivots that can be rotated about the pivots for implantation onto resected bone and a method for implanting same.

BACKGROUND OF THE INVENTION

Implants for joint replacement procedures such as a femoral implant used in total knee arthroplasty ("TKA") procedures have generally straight pegs, keels, and/or other projections for insertion into corresponding recesses in a distal femur to facilitate fixation of the implant. A surgeon typically prepares the implant receiving bone by utilizing surgical instrument(s) to cut a series of planar bone surface resections and make recesses in the bone to receive the projections. The planar bone resections and bone recesses are oriented to interface with flat surfaces and the projections formed on a bone engaging surface of the femoral implant such that the projections are generally aligned with the recesses and are generally perpendicular to the flat surfaces when the implant is operatively coupled to the prepared bone. An opposite side of the femoral implant includes an articulation surface that is preferably designed to articulate with a like articulation surface formed on an implant to be implanted on the other bone of the knee.

The femoral implant projections, which are present on both condylar surfaces of the implant, are generally designed for linear insertion into the corresponding recesses of the prepared bone. When the femoral implant is loaded along the axis of insertion, micromotion between the femoral implant and the prepared bone can occur. Micromotion can lead to loosening of the femoral implant and prevent osseointegration. Micromotion can be exacerbated when the axis of insertion is aligned with the overall leg in stance.

Planar cut implants are sometimes used in conjunction with cement or another fixation compound to guarantee a solid connection between the implants and the bone. One drawback in utilizing cements or the like is that the required cement layer often results in an unwanted transformation from a very precisely prepared surface to an imprecise prepared bone surface. This is largely due to the imprecise nature of working with cement. In a situation where a bone surface has been prepared to meet very specific dimensions, application of cement prior to implanting the implant will result in the surface exhibiting less than precise dimensions.

Therefore, there exists a need for a femoral implant that provides enhanced bone attachment to minimize or eliminate micromotion.

BRIEF SUMMARY OF THE INVENTION

In certain embodiments, the present disclosure relates generally to femoral implants with pivots and methods for implanting the same.

In an aspect of the present disclosure, a femoral implant with an articulating surface and a bone contacting surface is provided. In accordance with this first aspect, the bone contacting surface may include a first pivot pad, a first curved keel, a second pivot pad and a second curved keel. The first pivot pad may extend anteriorly from a posterior end of a first condylar surface. The first curved keel may extend proximally from the first condylar surface. The first curved keel may have a first curve defining a first radius. The second pivot pad may extend anteriorly from a posterior end of a second condylar surface spaced away from the first condylar surface. The second curved keel may extend proximally from the second condylar surface. The second curved keel may have a second curve defining a second radius. When the first and second pivot pads are placed in corresponding recesses on a resected distal bone, the femoral implant may be rotated about the first and second pivot pads to place the first and second curved keels into corresponding curved recesses on the resected distal bone.

Continuing in accordance with this aspect, the femoral implant may include an anterior surface having a third curved surface defining a third radius. The first, second and third curves may be concentric with a common center. The center may be located at or adjacent a posterior end of the femoral implant. The first radius may be equal to the second radius and less than the third radius such that when the first and second pivot pads are placed in the corresponding recesses on the resected distal bone, the first, second and third curves may be rotated along paths defined by the first, second and third radii respectively. The first and second pivot pads may be convex-shaped pads extending medial-laterally across the first and second condylar surfaces respectively. The first and second convex-shaped pads may describe first and second pad curves respectively. The first pad curve may define a first pad radius from the center and the second pad curve may describe a second pad radius from the center. The first pad radius may be equal to the second pad radius.

Continuing in accordance with this aspect, the bone contacting surface may be a concave surface.

In a further aspect according to the present disclosure, a femoral implant having an articular surface and a bone contacting surface is provided. In accordance with this second aspect, the bone contacting surface may include first and second ends, and first and second keels. The first and second ends may have first and second pivot pads for contacting corresponding resected distal bone recesses. The first and second keels may extend from the bone surface and may have first and second curves defining first and second radii respectively. When the first and second pivot pads contact the corresponding recesses on the resected distal bone, the femoral implant may be rotated about the first and second pivot pads to place the first and second keels into corresponding curved recesses on the resected distal bone.

Continuing in accordance with this aspect, the femoral implant may include an anterior surface having a third curved surface. The first, second and third curves may be concentric with a common center. The center may be located at or adjacent a posterior end of the femoral implant. The first and second pivot pads may be convex-shaped pads extending medial-laterally across a first and second condylar surfaces respectively. The first and second condylar surfaces may be spaced apart. The first and second convex-shaped pads may describe first and second pad curves respectively. The first pad curve may define a first pad radius from the center, and the second pad curve may describe a second pad radius from the center. The first pad radius may be equal to the second pad radius. The bone contacting surface may be a concave surface.

In a further aspect of the present disclosure is a method of implanting a femoral implant on a resected distal bone. A method in accordance with this aspect may include the steps of placing first and second pivot pads of the femoral implant in corresponding first and second recesses on the resected distal bone, and rotating the femoral implant about the first and second pivot pads such that first and second curved keels are positioned into corresponding first and second curved recesses on the resected distal bone. The first and second pivot pads may extend anteriorly from posterior ends of first and second condylar surfaces respectively. The first and second condylar surfaces may be placed apart and may have first and second curved keels extending proximally from therein respectively.

Continuing in accordance with this aspect, the step of rotating the femoral implant may include rotating an anterior surface of the femoral implant to contact an anterior portion of the resected distal bone. The anterior surface may define a third curve such that rotating the femoral implant about the first and second pivot pads traverses a leading edge of the anterior surface along a path defined by the third curve.

In a further aspect of the present disclosure, a femoral implant with an articulating surface and a bone contacting surface is provided. In accordance with this first aspect, the bone contacting surface may include a first pivot pad, a first curved keel, and a second curved keel. The first pivot pad may extend anteriorly from a posterior end of a first condylar surface. The first curved keel may extend proximally from the first condylar surface. The first curved keel may have a first curve defining a first radius. The second curved keel may extend proximally from the second condylar surface. The second curved keel may have a second curve defining a second radius. When the first pivot pad is placed in corresponding recess on a resected distal bone, the femoral implant may be rotated about the first pivot pad to place the first and second curved keels into corresponding curved recesses on the resected distal bone.

Continuing in accordance with this aspect, the femoral implant may include an anterior surface having a third curved surface defining a third radius. The first, second and third curves may be concentric with a common center. The center may be located at or adjacent a posterior end of the femoral implant. The first radius may be equal to the second radius and less than the third radius such that when the first pivot pad is placed in the corresponding recess on the resected distal bone, the first, second and third curves may be rotated along paths defined by the first, second and third radii respectively. The first pivot pad may be convex and extend medial-laterally across one of the first and second condylar surfaces.

Continuing in accordance with this aspect, the femoral implant may further include a second pivot pad extending anteriorly from a posterior end of the other of the first and second condylar surfaces. The first and second pivot pads may be convex and extend medial-laterally across the first and second condylar surfaces. The first and second pivot pads may describe first and second pad curves respectively. The first pad curve may define a first pad radius from the center and the second pad curve may describe a second pad radius from the center. The first pad radius may be equal to the second pad radius.

Continuing in accordance with this aspect, the bone contacting surface may be a concave surface.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention. As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Reference will now be made in detail to the various embodiments of the present disclosure illustrated in the accompanying drawings. Wherever possible, the same or like reference numbers will be used throughout the drawings to refer to the same or like features. It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described. As used herein, the terms "peg," "keel" and "post" will be used interchangeably and as such, unless otherwise stated, the explicit use of either term is inclusive of the other term. Similarly, the terms "aperture," "hole," and "recess" will be used interchangeably and as such, unless otherwise stated, the explicit use of either term is inclusive of the other term.

Figure 1:
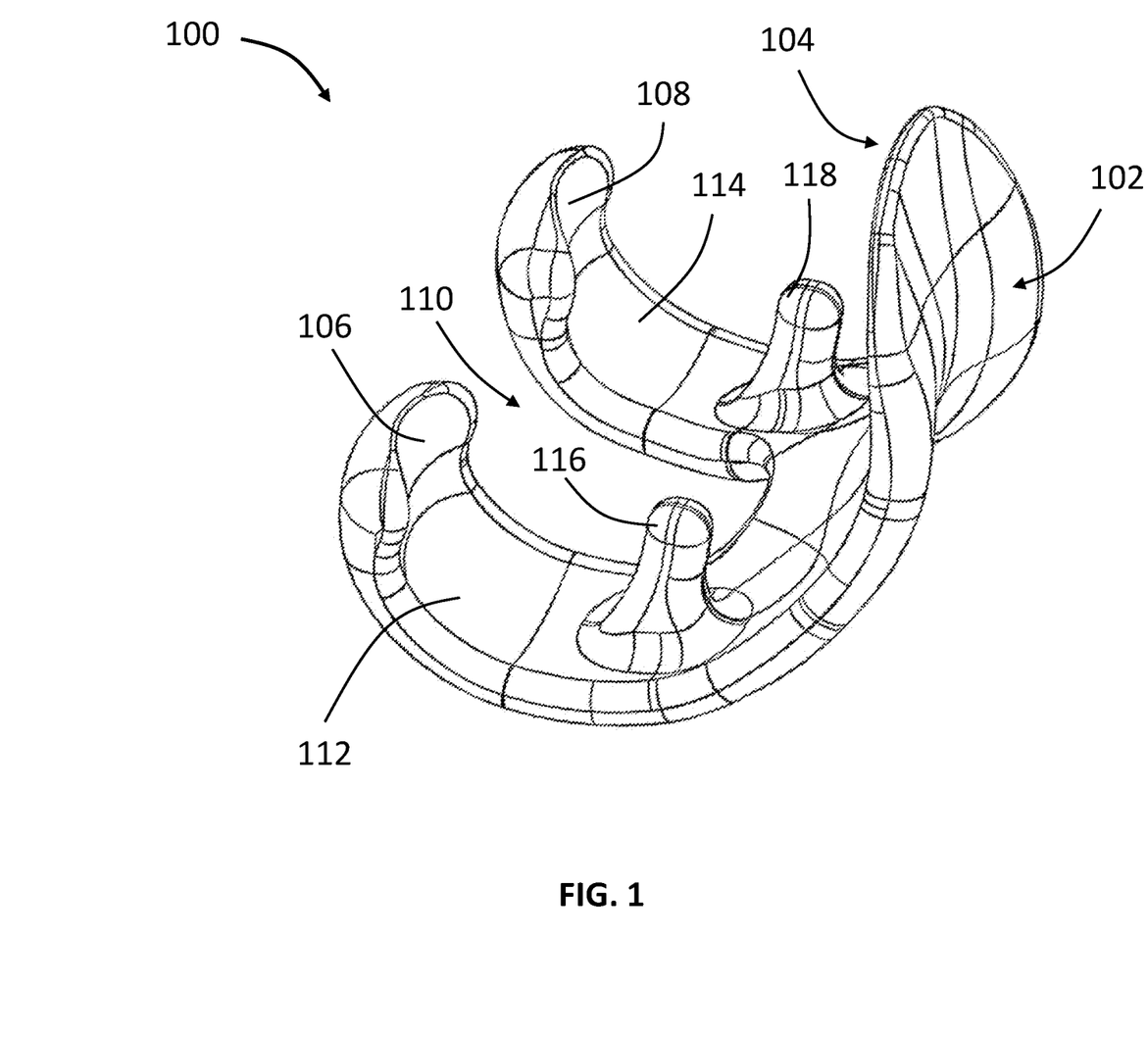
FIG. 1 is a perspective view of a femoral implant in accordance with an embodiment of the present disclosure.
Figure 2:
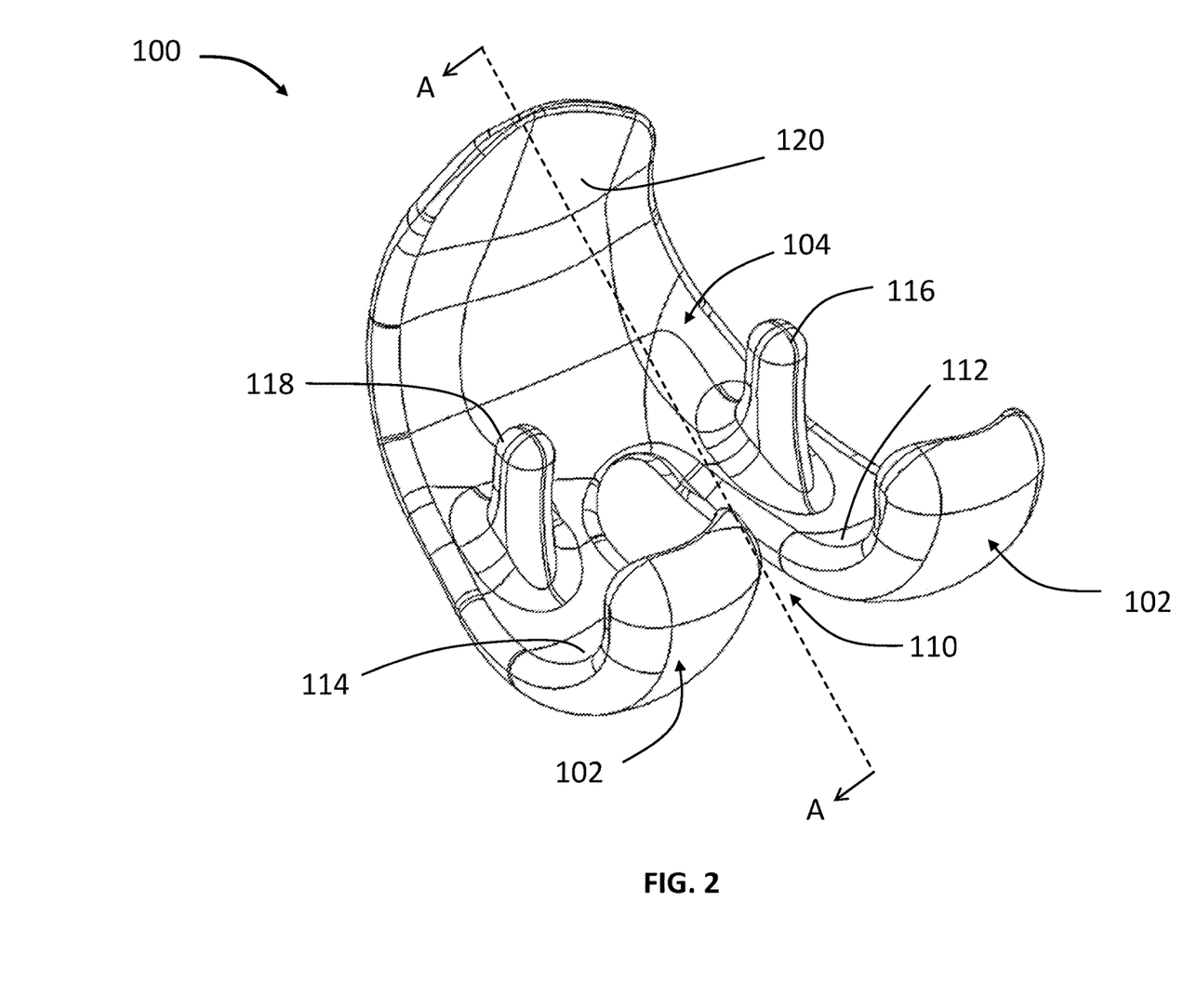
FIG. 2 is a another perspective view of the femoral implant of FIG. 1.

Referring to FIGS. 1 and 2, there are shown perspective views of a femoral implant 100 for a distal end of a femur according to an embodiment of the present disclosure. Femoral implant 100 has an outer articulating surface 102 and an opposing inner bone contacting surface 104. Outer articulating surface 102 includes an articular condyle surface having a pair of laterally spaced-apart articular posterior condyle surfaces. The outer articular surface is curved to correspond to the convex curvature of a femoral condyle. Bone contacting surface 102 includes a medial condylar surface 112 and a lateral condylar surface 114 separated by an intercondylar notch 110. While articulating surface 102 and bone contacting surface 104 are generally curvate in this embodiment, other embodiments may be only partially curvate. A medial pivot pad 106 and a lateral pivot pad 108 are included at the posterior ends of medial condylar surface 112 and lateral condylar surface 114, respectively, as best shown in FIG. 1. A curved medial keel 116 and a lateral keel extend from medial condylar surface 112 and lateral condylar surface 114, respectively. The anterior portion of bone contacting surface 104 includes an anterior surface 120.

Figure 3:
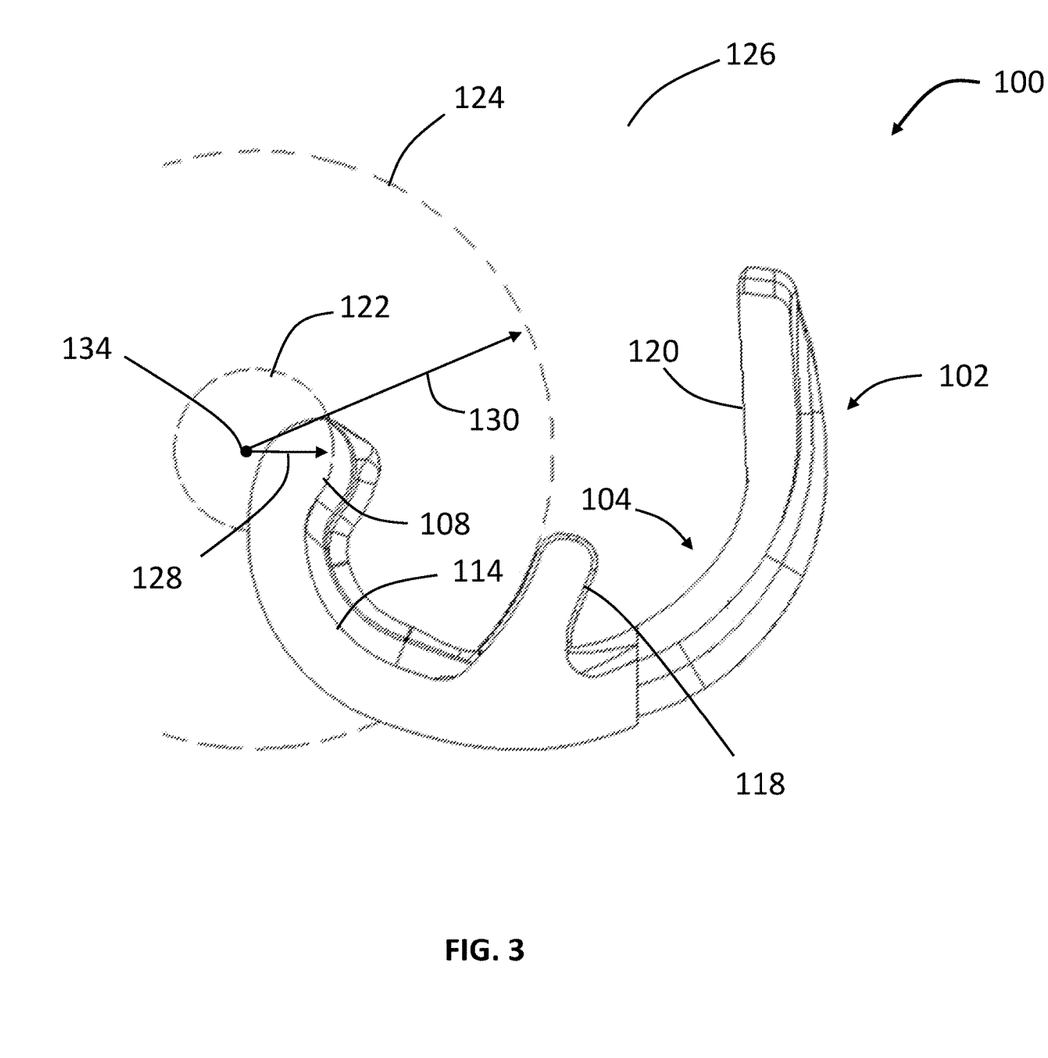
FIG. 3 is side cross-sectional view of the femoral implant of FIG. 1 along line A-A.

FIG. 3 shows a side perspective of femoral implant 100 along line A-A of FIG. 2. Posterior ends of lateral condylar surface 114 and medial condylar surface 112 include a lateral pivot pad 108 and a medial pivot pad 106, respectively. Pivot pads 106, 108 extend anteriorly from their respective condylar surfaces to define concave profiles when viewed in a medial-lateral as best shown in FIG. 3, and convex profiles when viewed in a superior-inferior direction as best shown in FIG. 2. The concave-convex profiles of pivot pads 106, 108 form saddle-shaped pads that facilitate not just rotation of femoral implant 100 around these pivot pads, but also ensure that these pivot pads remain seated in corresponding recesses during rotation. As shown in FIG. 3, lateral keel 118 and lateral pivot pad 108 define circular curves. Lateral keel 118 defines a lateral keel curve 124 with a radius 130 and lateral pivot pad defines a lateral pad curve 122 with a radius 128. Lateral keel curve 124 and lateral pad curve 122 form concentric circles with a center 134 as best shown in FIG. 3. Medial keel 116 defines a medial keel curve (not shown) similar to lateral keel curve 124, and medial pivot pad 106 defines a medial pad curve (not shown) similar to lateral keel curve 124. Center 134 is positioned slightly away from a posterior end of lateral condylar surface 114 to achieve the required radii for the keel and pad curves. While femoral implant 100 has circular pad and keel curves, other embodiments can have various other pad and keel curve profiles such as elliptical, parabolic, hyperbolic, cubic parabola, etc. profiles. The position of center 134 can also be varied to generate the required pad and keel curves. Center 134 can be a common singular point for the lateral and medial sides of femoral implant as shown in FIG. 3. In another embodiment, the medial side can have a medial-side center and the lateral side can have a lateral side center for their respective keel and pivot pad curves. While saddle-shaped pivot pads are shown in femoral implant 100, other shapes can be used in other embodiments. For example, the pivot pad can include a protrusion, rib, sharp point, edge, etc. in other embodiments.

Figure 4:
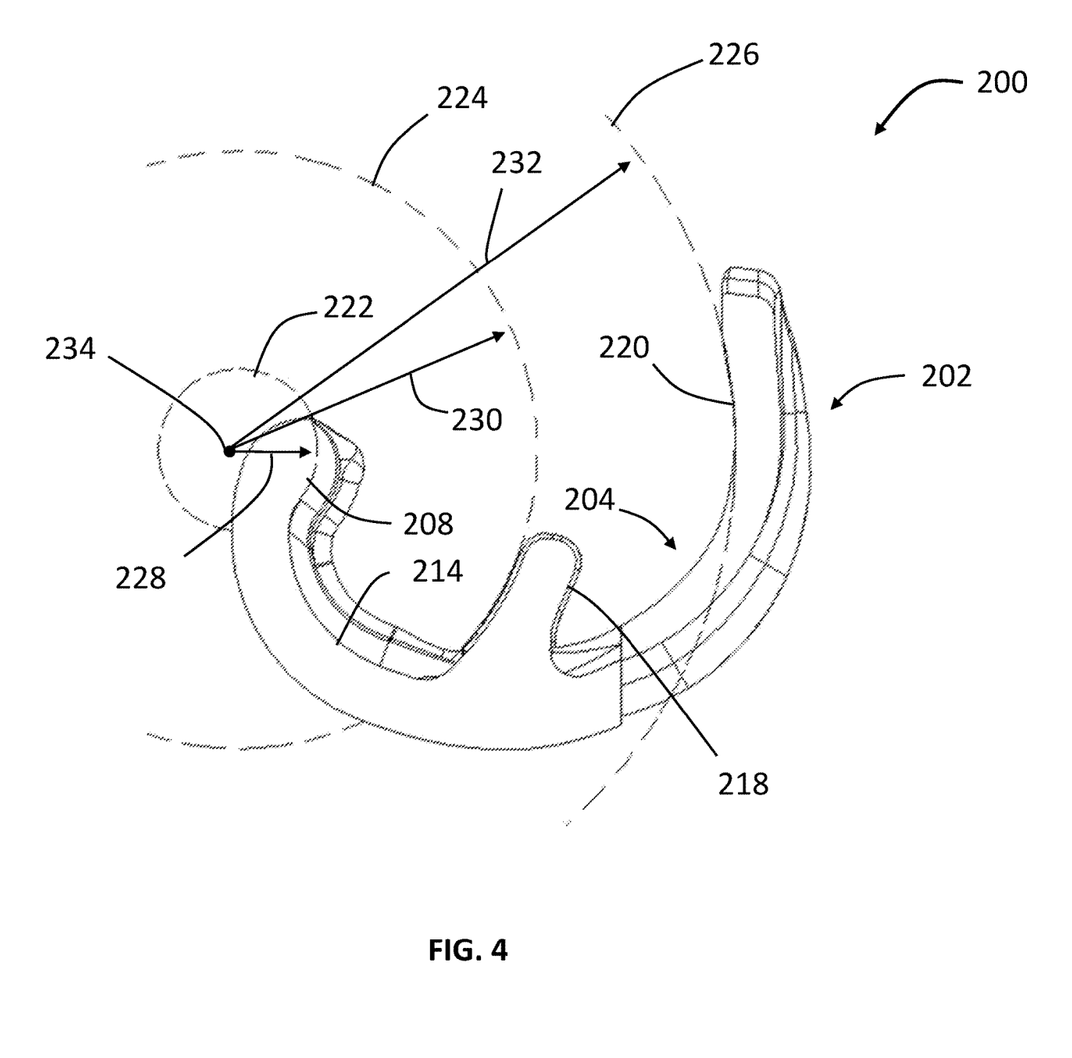
FIG. 4 is a side cross-sectional view of a femoral implant according to another embodiment of the present disclosure.

Referring now to FIG. 4, there is shown a side cross-sectional view of a femoral implant 200 according to another embodiment of the present disclosure. Femoral implant 200 is similar to femoral implant 100, and therefore like elements are referred to with similar numerals within the 200-series of numbers. For example, femoral implant includes a bone contacting surface 204 with a curved lateral keel 218 extending from a lateral condylar surface 214. However, femoral implant 200 includes an anterior surface 220 defining an anterior surface curve 226 with a radius 232 from center 234. As shown here, the anterior surface curve 226 is concentric with lateral keel curve 224 and lateral pad curve 222. The curved profile of anterior surface 220 eliminates or reduces bone contact between anterior surface 220 and distal femur during insertion as more fully explained below.

Figure 5:
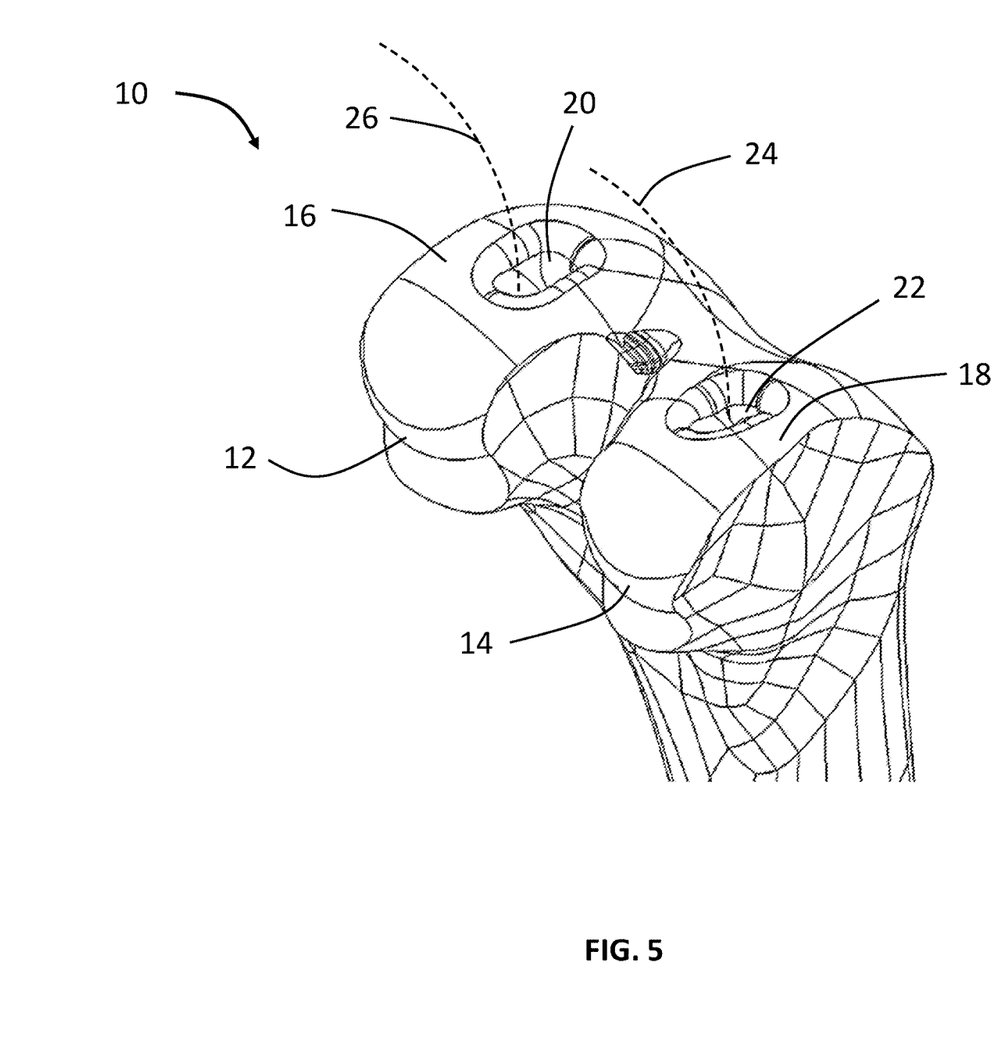
FIG. 5 is a perspective view of a resected distal femur.

FIG. 5 shows a resected distal femur 10 prepared to receive femoral implant 100. Bone contacting surface 104 of femoral implant 100 conforms to the outer surface of resected distal femur 10 to ensure proper fit of the femoral implant with the resected distal femur. A medial groove or notch 12 and a lateral groove or notch 14 are made on a medial condylar surface 16 and a lateral condylar surface 18, respectively. Medial notch 12 and lateral notch 14 are shaped and sized to receive and allow the saddle-shaped medial and lateral pivot pads to pivot within these notches, respectively. As explained above, the saddle-shaped pivot pads 106, 108 are configured to engage with medial and lateral notches 12, 14, respectively, to allow for rotation of femoral implant 100 around these pivot pads and to ensure that these pivot pads remain seated firmly in the lateral and medial notches during rotation. This allows a surgeon or an operator to conveniently rotate femoral implant 100 about these pivot pads once they are placed in their respective notches on resected distal femur 10. A medial aperture 20 is formed on medial condylar surface 16 and a lateral aperture 22 is formed on lateral condylar surface 18. Medial aperture 20 and lateral aperture 22 are sized and shaped to receive the medial and lateral keels respectively. The depth and curve of the medial and lateral apertures conforms to the medial and lateral keels, respectively. The medial aperture defines a medial aperture curve 26 that matches the medial keel curve. Similarly, the lateral aperture defines a lateral aperture curve 24 that matches lateral keel curve 124. The corresponding dimensions and shape profiles between resected distal femur 10 and femoral implant 100 allow for convenient implantation and secure attachment of the femoral implant to the resected bone as more fully disclosed below.

Figure 6:
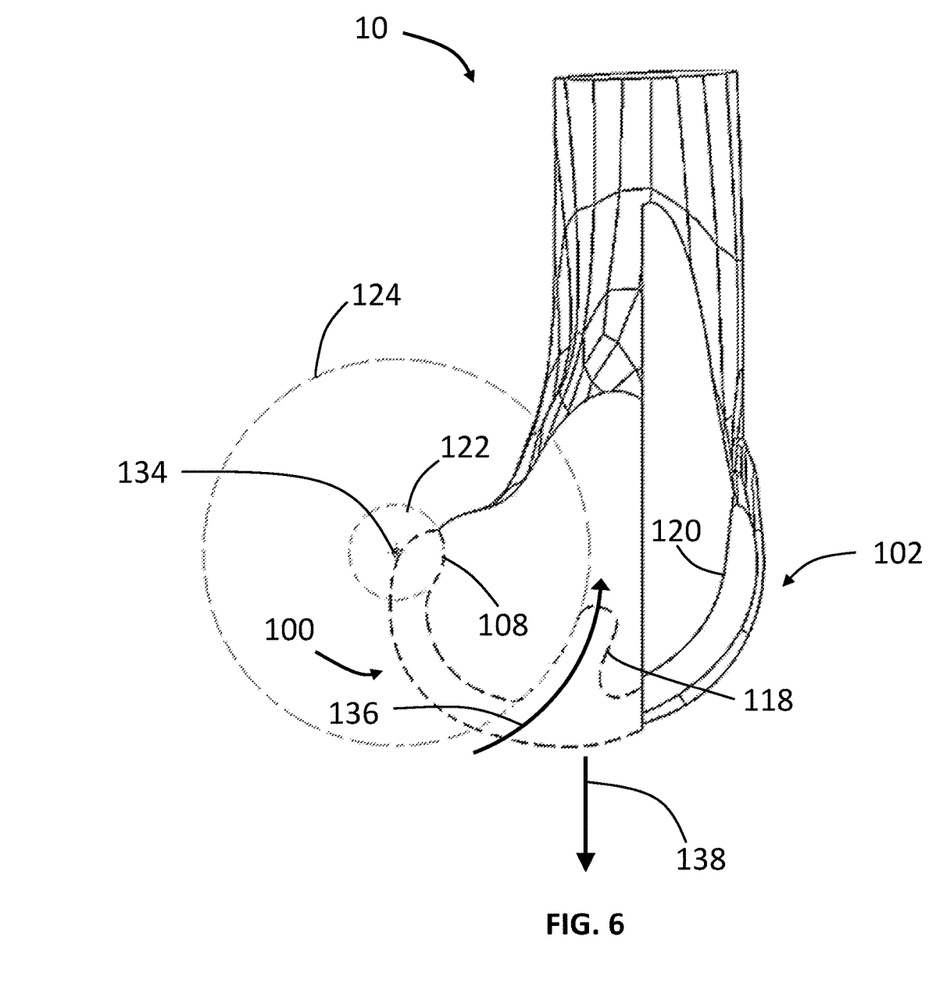
FIG. 6 is a partial side cross-sectional view of the femoral implant of FIG. 1 implanted on the resected distal femur of FIG. 5, and FIGS. 7A-7C are partial side cross-sectional views showing the sequential steps of attaching the femoral implant of FIG. 1 on the resected distal femur of FIG. 5.

FIG. 6 shows a partial side cross-sectional view of femoral implant 100 implanted on resected distal femur 10. A curved insertion path 136 of lateral keel 118 into lateral aperture 22 aligns with the lateral keel curve and the lateral pad curve. Similarly, medial keel 116 traces a curved insertion path (not shown) into medial aperture 20. Femoral implant 100 is implanted onto resected distal femur 10 by rotating the implant about the lateral and medial pivot pads to move the lateral and medial keels along their respective curved insertion paths into the lateral and medial apertures, respectively. Once femoral implant 100 is secured to distal femur 10 as shown in FIG. 6, separation of femoral implant 100 from distal femur 10 requires that the medial and lateral keels move along the curved insertion paths. Physiological loads on femoral implant 100 which act normal to the femoral implant surface will not separate the femoral implant from the distal femur. For example, load vector 138 shown in FIG. 6 will not separate femoral implant 100 from the distal femur 10 as the curved keel insertion/extraction paths will prevent the femoral implant from moving linearly along load vector 138. Thus, the curved medial/lateral keels, curved medial/lateral pivot pads of femoral implant 100 will facilitate convenient implantation of the implant and prevent micromotion between the femoral implant and the distal femur to enhance attachment. Keel length and keel curve can be configured to optimize bone attachment. For example, larger keel lengths will increase load bearing capacity of the keels thereby increasing resistance to micromotion, whereas reduced keel lengths will require less bone removal from the apertures. A larger keel curve—i.e., larger curve radius, will facilitate more convenient bone removal from the apertures. As shown in FIG. 6, apertures 20, 22 are sized to create an interference fit with keels 116, 118, respectively, so that the keels are ultimately tightly fit therein. Of course, in other embodiments, the apertures may be created larger than the keels. It should be understood that although apertures 20, 22 are shown and described as being formed in the bone, such structures may vary depending upon the particular configuration of the implants.

Figure 7A:
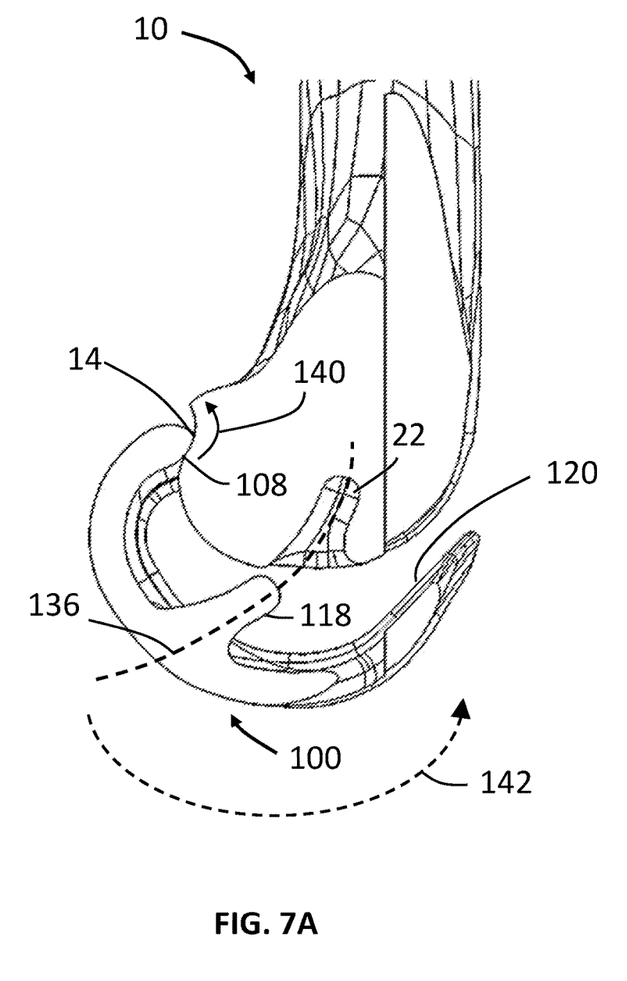
Figure 7B:
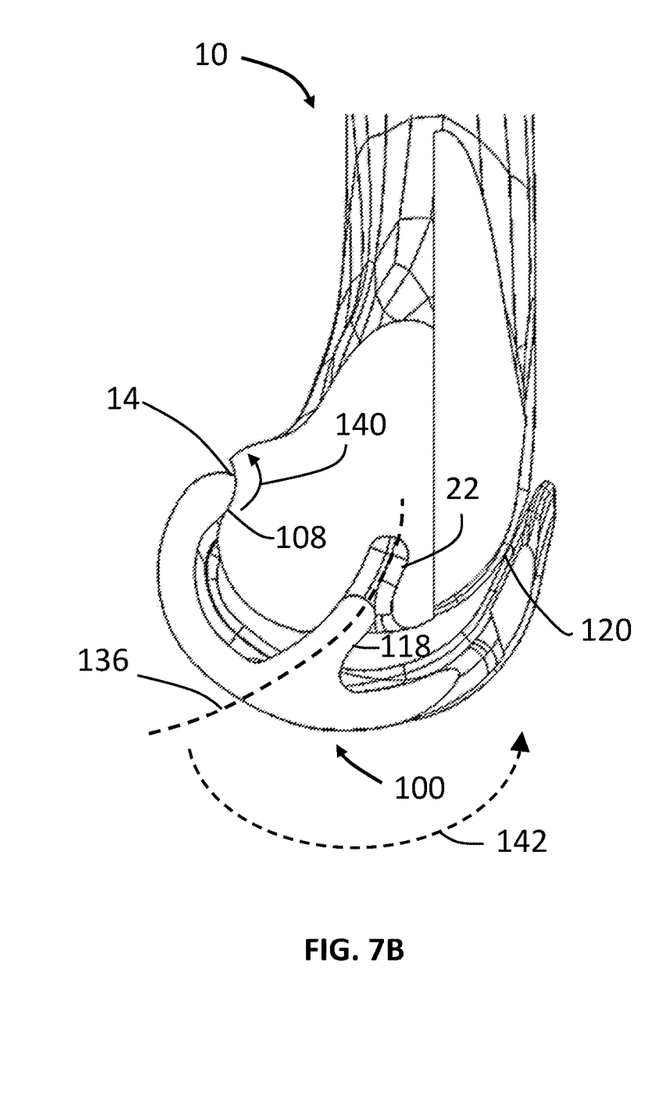
Figure 7C:
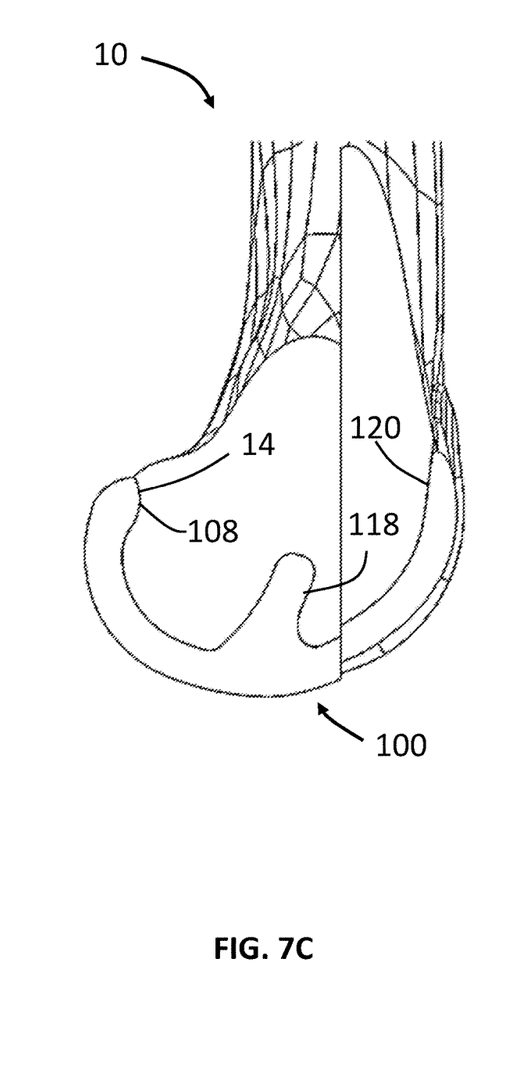

Referring now to FIGS. 7A-7C, there are shown partial side cross-sectional views of sequential steps for attaching femoral implant 100 to resected distal femur 10. While FIGS. 7A-7C show only the lateral side of femoral implant 100 and distal femur 10 including lateral notch 14, lateral pivot pad 108 and lateral keel 118, the medial side of femoral implant 100 and distal femur 10 undergo similar interactions between the femoral implant 100 and distal femur 10 as described below. Thus, it should be understood that interactions between femoral implant 100 and distal femur 10 depicted in FIGS. 7A-7C and described below with regard to the lateral side of femoral implant 100 and distal femur 10 also apply to the medal side of femoral implant 100 and distal femur 10.

As shown in FIG. 7A, medial pivot pad 106 and lateral pivot pad 108 of femoral implant 100 are first positioned in medial notch 12 and lateral notch 14 of distal femur 10, respectively. Femoral implant 100 is then rotated about the medial and lateral pivot pads as shown by direction arrow 142. As femoral implant 100 is rotated about the medial and lateral pivot pads, medial and lateral keels 116, 118 follow their respective keel insertion paths (lateral keel insertion path 136 shown in FIG. 7A) in preparation to enter the medial and lateral apertures, respectively. The curved shapes of the medial and lateral pivot pads allow these pivot pads to slide along direction 140 as femoral implant 100 is rotated along direction arrow 142.

As femoral implant 100 is rotated along direction arrow 142, lateral keel 118 enters lateral aperture 22 along lateral keel insertion path 136 as shown in FIG. 7B. Similarly, the medial keel 116 enters medial aperture 20 along the medial keel insertion path. Anterior surface 120 wraps around the anterior portion of distal femur 20. While anterior portion 120 of femoral implant 100 contacts the anterior portion of distal femur 20 during implantation, the curved anterior portion 220 of femoral implant 200 described above, is shaped to minimize or prevent contact with the anterior portion of distal femur 10 during implantation. Thus, the curved anterior portion of femoral implant 200 requires less bone contact, and consequently less effort during implantation onto distal femur 10. Also, as seen in FIG. 7B, lateral pivot pad 108 moves proximally further into lateral notch 14 as femoral implant 100 is rotated.

FIG. 7C shows an implanted femoral implant 100 establishing full contact between bone contacting surface 104 and distal femur 10. In this position, medial and lateral keels 116, 118 are firmly secured within the medial and lateral apertures 20, 22 of distal femur. Anterior surface 120 contacts the anterior portion of distal femur 10. The medial and lateral pivot pads 106, 108 are fully seated within the medial and lateral notches 12, 14. As described above, physiological loads on femoral implant 100 which act normal to the femoral implant surface will not separate the femoral implant from the distal femur once implantation is compete as shown in FIG. 7C.

The femoral implant of the present disclosure can be implanted in conjunction with cement or another fixation compound to guarantee a solid connection between the implants and the bone. The femoral implants of the present disclosure may be, but are not limited to being, made of any polymer such as PEEK, carbon fiber reinforced PEEK, PAEK, UHMWPE, metals, ceramics, combinations of the foregoing, or other suitable materials that are biocompatible and possess sufficient strength and rigidity.

It should be understood that although specific structures such as keels 116, 118 and pivot pads 106, 108 are depicted in the drawings and described herein, other structures are indeed contemplated, including the use of spikes, pegs, and the like. Whereas a femoral implant is described here, the present disclosure can be utilized for other implants such as, but not limited to, hip implants, spinal implants and dental implants.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made and are encouraged to be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A monolithic femoral implant having an articulating surface and a bone contacting surface, the bone contacting surface comprising:
   a first curved keel extending proximally from a first condylar surface, the first curved keel having a first curve defining a first radius;
   a second curved keel extending proximally from a second condylar surface, the second curved keel having a second curve defining a second radius;
   a first pivot pad extending anteriorly from a posterior end the first condylar surfaces; and a second pivot pad extending anteriorly from a posterior end of the second condylar surface,
   wherein when the first pivot pad is placed in a corresponding recess in a resected distal bone, the femoral implant can be rotated about the first pivot pad to place the first curved keel into a curved medial recess of the resected distal bone and the second curved keel into a curved lateral recess of the resected distal bone.

2. The femoral implant of claim 1, wherein the femoral implant includes an anterior surface having a third curved surface defining a third radius.

3. The femoral implant of claim 2, wherein the first and third curves are concentric with a common center.

4. The femoral implant of claim 3, wherein the first radius is equal to the second radius and less than the third radius such that when the first pivot pad is placed in the corresponding recess on the resected distal bone, the first, second and third curves can be rotated along paths defined by the first, second and third radii respectively.

5. The femoral implant of claim 4, wherein the first pivot pad is convex and extends medial-laterally across the one of the first and second condylar surfaces.

6. The femoral implant of claim 1, wherein the first and second pivot pads are convex and extend medial-laterally across the first and second condylar surfaces respectively.

7. The femoral implant of claim 6, wherein the first and second pivot pads have first and second pad curves respectively, the first pad curve defining a first pad radius and the second pad curve describing a second pad radius.

8. The femoral implant of claim 7, wherein the first pad radius is equal to the second pad radius.

9. The femoral implant of claim 1, wherein the bone contacting surface further includes a concave surface.

10. A monolithic femoral implant having an articulating surface and a bone contacting surface, the bone contacting surface comprising:
   first and second ends having first and second pivot pads respectively for contacting corresponding resected distal bone recesses, and first and second keels extending from the bone contacting surface and having first and second curves defining first and second radii respectively, wherein when the first and second pivot pads contact the corresponding recesses on the resected distal bone, the femoral implant can be rotated about the first and second pivot pads to place the first and second keels into corresponding curved recesses on the resected distal bone, wherein the first and second pivot pads are convex-shaped pads extending medial-laterally across first and second bone contacting surface portions respectively, the first and second bone contacting surface portions being spaced apart.

11. The femoral implant of claim 10, wherein the femoral implant includes an anterior surface having a third curved surface.

12. The femoral implant of claim 11, wherein the first and third curves are concentric with a common center.

13. The femoral implant of claim 12, wherein the center is located at or adjacent a posterior end of the femoral implant.

14. The femoral implant of claim 10, wherein the first and second convex-shaped pads describe first and second pad curves respectively, the first pad curve defining a first pad radius and the second pad curve describing a second pad radius.

15. The femoral implant of claim 14, wherein the first pad radius is equal to the second pad radius.

* * * * *